United States Patent
Park et al.

(10) Patent No.: US 9,480,638 B2
(45) Date of Patent: Nov. 1, 2016

(54) **COSMETIC COMPOSITION CONTAINING EXTRACTS OF *ADENOPHORA TRIPHYLLA VAR. JAPONICA HARA, ANGELICA TENUISSIMA* AND MEDICINAL HERBS**

(75) Inventors: Jun Seong Park, Suwon-si (KR); Dong Hyun Kim, Suwon-si (KR); Nok Hyun Park, Yongin-si (KR); Hye Yoon Park, Anyang-si (KR); Jae Kyoung Lee, Seoul (KR); Duck Hee Kim, Seoul (KR); Han Kon Kim, Suwon-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 938 days.

(21) Appl. No.: 13/129,932

(22) PCT Filed: Nov. 19, 2009

(86) PCT No.: PCT/KR2009/006839
§ 371 (c)(1),
(2), (4) Date: May 18, 2011

(87) PCT Pub. No.: WO2010/058986
PCT Pub. Date: May 27, 2010

(65) Prior Publication Data
US 2011/0223268 A1 Sep. 15, 2011

(30) Foreign Application Priority Data
Nov. 19, 2008 (KR) .................. 10-2008-0115260

(51) Int. Cl.
*A61K 8/97* (2006.01)
*A61Q 19/00* (2006.01)
(52) U.S. Cl.
CPC .............. *A61K 8/97* (2013.01); *A61Q 19/00* (2013.01); *A61K 2800/522* (2013.01)
(58) Field of Classification Search
None
See application file for complete search history.

(56) References Cited

FOREIGN PATENT DOCUMENTS

| JP | 2003113013 A | * | 4/2003 |
| KR | 2001070388 A | * | 7/2001 |
| KR | 2006093164 A | * | 8/2006 |

OTHER PUBLICATIONS

AAAS 1995, http://ip.aaas.org/tekindex.nsf/2a9c4e44835b04ea85256a7200577a64/25c0eecac8a81cf385256ae700755f2d/Body/M1?OpenElement.*
International Search Report for PCT/KR2009/006839, mailed Aug. 9, 2010.
Written Opinion of the International Searching Authority for PCT/KR2009/006839, mailed Aug. 2010.
Choi, H-J. et al., "Effects of adenophora triphylla ethyl acetate extract on mRNA levels of antioxidant enzymes in human HepG2 cells", J. Korean Soc. Food Sci. Nutr., (Oct. 31, 2008), vol. 37(10), pp. 1238-1243.
Lee, H-J. et al., "Antioxidant and nicotine degradation effects of medicinal herbs", J. Food Sci. Nutr., (2003), vol. 8, pp. 289-293.
Jeong, C-S. et al., "Protective effects of Angelica tenuissima Nakai on Hepatotoxicity by Carbon Tetrachloride in Rats", The Journal of Applied Pharmacology, (2002), vol. 10, pp. 211-217.
Chung, I-M et al., "Screening of Korean Medicinal and Food Plants with Antioxidant Activity", Korean J. Medicinal Crop Sci., (1998), vol. 6(4), pp. 311-312.

* cited by examiner

*Primary Examiner* — Terry A McKelvey
*Assistant Examiner* — Catheryne Chen
(74) *Attorney, Agent, or Firm* — Nixon & Vanderhye PC (57) ABSTRACT

Disclosed herein is a cosmetic composition containing, as an active ingredient, a mixture of extracts of honey-roasted *Adenophora triphylla* var. *japonica* Hara and honey-roasted *Angelica tenuissima* Nakai, processed using a medicinal herb processing technique, and of extracts of medicinal herbs such as *Lycium chinense* Mill or *Paeonia suffruticosa*, and thus shows excellent antioxidant and skin-moisturizing effects.

14 Claims, 2 Drawing Sheets

COSMETIC COMPOSITION CONTAINING EXTRACTS OF *ADENOPHORA TRIPHYLLA* VAR. *JAPONICA* HARA, *ANGELICA TENUISSIMA* AND MEDICINAL HERBS

This application is the U.S. national phase of International Application No. PCT/KR2009/006839, filed 19 Nov. 2009, which designated the U.S. and claims priority to KR Application No. 10-2008-0115260, filed 19 Nov. 2008, the entire contents of each of which are hereby incorporated by reference.

TECHNICAL FIELD

The present invention relates to a cosmetic composition containing, as an active ingredient, a mixture of extracts of honey-roasted *Adenophora triphylla* var. *japonica* Hara and honey-roasted *Angelica tenuissima* Nakai, processed using a medicinal herb processing technique, and of extracts of medicinal herbs such as *Lycium chinense* Mill or *Paeonia suffruticosa*, and thus shows excellent antioxidant and skin-moisturizing effects.

BACKGROUND ART

A traditional Chinese medicine manufacturing technique using a medicinal herb processing technique is called "Po-je", "Hap-hwa", "Hap-yak", "Su-chi", "Po-ja", "Beob-je" and "Su-sa" in Korean. This medicine manufacturing technique comprises changing the inherent properties of medicinal herbs by processing the medicinal herbs on the basis of Chinese medicine theory.

The objects of processing medicinal herbs are to clarify medicine, facilitate the storage of medicines, reduce or remove the toxicity or side effects of medicines, change the properties of medicines to make the medicines more effective, enhance the therapeutic effects of medicines, and eliminate offensive odors and tastes of medicines to facilitate the intake of the medicines.

In the manufacture of cosmetic products, raw materials having various effects, including skin whitening, wrinkle reduction and skin protection, are screened and added. An antioxidant effect removes reactive oxygen species, which are the cause of skin aging, to retard or prevent skin aging, makes a dark and inelastic skin fresh and clear, and makes the skin appear healthy. However, only a limited number of materials are known to have the antioxidant effect, and only a small number of the materials that are currently used are chemically synthesized.

The skin functions as an important barrier to protect the body from external factors. The barrier function is a protective function to defend the body from various external stimuli, for example chemicals, atmospheric pollutants, dry environments and UV rays, and to prevent anexcessive loss of water from the body through the skin. This protective function can be maintained when the horny layer consisting of keratinocytes is maintained in a normal state.

The horny layer (stratum corneum), which is the outermost layer of the epidermis, is formed from keratinocytes and consists of differentiated keratinocytes and lipid layers surrounding these keratinocytes (Marcelo C. L. et al, J. Invest. Dermatol., 80, pp 37-44, 1983).

Keratinocytes are characteristic cells formed as a result of a process in which basal cells that continuously proliferate in the basal layer of the epidermis are pushed up to the surface of the skin while undergoing gradual changes in their shape and function. After the passage of a given period of time, old keratinocytes are shed from the skin's surface, and new keratinocytes function in place of the shed cells. This repeated and serial process is called differentiation or keratinization of epidermal cells.

Further, during the keratinization process, keratinocytes produce natural moisturizing factors (NMFs) and intracellular lipids (ceramides, cholesterols, fatty acids, etc.) while forming a horny layer, which impart solidity and flexibility to the horny layer that consequently will function as the skin barrier.

However, the horny layer is highly susceptible to functional loss by various factors, for example living and behavioral factors such as excessive face washing and bathing, environmental factors such as dry atmosphere, contaminants, etc., and endogenous disorders such as atopic dermatitis and senile pruritus. With recent substantial increases of various harmful factors, the number of patients who complain of dry skin conditions and consequential disorders has gradually increased.

Accordingly, various studies focused on supplying water from an external source or preventing the loss of water from the body to maintain the skin's water content at a suitable level have been conducted, and various moisturizers having water-holding capacity have been developed. Lipid components such as ceramides, and materials capable of increasing water retention in the horny layer, such as essential fatty acids and lipid complexes, are generally used as skin moisturizers (Rawlings A. V. et al, J. Invest. Dermatol., 5, pp 731-741, 1994).

However, currently, factors harmful to the skin are gradually increasing, production and shedding rates of the horny layer are becoming slower due to a change of eating habits, and the amount of moisturizing factors and lipids is decreasing due to deterioration in the function of keratinocytes. For these reasons, more people have a skin whose horny layer does not exhibit a normal skin barrier function. This deterioration of the skin barrier function leads to various skin diseases, including xerosis cutis, a topic dermatitis, contact dermatitis and psoriasis. Although such diseases can be alleviated with conventional moisturizers having water-holding capacity, the diseases are difficult to fundamentally cure.

Recently, various cosmetic products that employ natural materials in order to reduce skin irritation caused by various chemical substances have been developed. In addition, natural materials having reduced side effects on the skin receive a great deal of attention from consumers. Thus, many efforts are being made to develop natural materials useful as cosmetic raw materials.

DISCLOSURE OF INVENTION

Technical Problem

Accordingly, the present inventors have conducted studies to solve the above-mentioned problems occurring in the prior art and to find raw materials having improved antioxidant and skin moisturizing effects and, as a result, have found that a mixture of extracts of honey-roasted *Adenophora triphylla* var. *japonica* Hara, honey-roasted *Angelica tenuissima* and medicinal herbs such as *Lycium chinense* Mill. and *Paeonia suffruticosa* Andrews has excellent antioxidant and skin-moisturizing effects, and have thereby completed the present invention.

An object of the present invention is therefore to provide a cosmetic composition containing extracts of processed medicinal herbs and extracts of medicinal herbs that shows excellent antioxidant and skin-moisturizing effects.

Solution to Problem

The cosmetic composition of the present invention contains, as an active ingredient, a mixture of extracts of honey-roasted *Adenophora triphylla* var. *japonica* Hara and honey-roasted *Angelica tenuissima*.

In addition, the cosmetic composition of the present invention may further contain an extract of at least one of *Lycium chinense* Mill. and *Paeonia suffruticosa* Andrews in addition to said mixture.

Hereinafter, the present invention is described in detail.

*Adenophora triphylla* var. *japonica* Hara (or as alternatives, *Adenophora polyantha* Naka, *Adenophora triphylla* var. *hirsuta* Naka, *Adenophora lilifolia* Ledeb., *Adenophora stricta* Miq., *Adenophora taquetii* Lev., or *Adenophora palustris* Kom.) used in the present invention has an extended cylindrical form and is curved, and has root branches in some cases. The rhizome is marked with whorled lateral wrinkles in the upper part. The outer surface of the root is pale yellowish white to pale grayish brown in colour, and has the distinct lateral wrinkles in the upper part and both longitudinal and lateral wrinkles in the lower part. The root is light and easy to snap off. The snapped surface is milky white with many pores.

*Angelica tenuissima* Nakai (or as alternatives, *Ligusticum sinense* Oliv, or *Ligusticum jeholense* Nakai et Kitagaw) used in the present invention has an irregular, exended cylindrical form having splits, and has tip marks remaining on the root head. The outer surface is grayish brown in colour and hard. The snapped surface is yellowish white with a rough surface, and is sometimes empty in the center. It has a characteristic smell and a hot taste.

*Paeonia suffruticosa* Andrews (or as alternatives, *Paeonia suffruticosa* var. *spontanea* Rehd, or *Paeonia szechuanica* Fang.) used in the present invention is a tubular or semi-tubular bark. The outer surface is dark brown to purple brown in colour and has long and small oval root marks along the transverse direction and longitudinal wrinkles, and the inner surface is pale grayish brown to dark purple in colour and flattened. The snapped surface is rough. The inner surface and the snapped surface have white crystals attached thereto.

*Lycium chinense* Mill. (or as an alternative, *Lycium barbarum* L.) used in the present invention has a tubular or semi-tubular form. The outer surface is yellow to grayish brown, and the inner surface is gray to grayish brown. The periderm is scale-shaped and easily peeled off. The snapped surface is grayish white to grayish brown in colour and coarse without fibers. The texture is light.

The method for preparing extracts used in the present invention is described hereinafter.

a) Step of Processing Medicinal Herbs

*Adenophora triphylla* var. *japonica* Hara and *Angelica tenuissima* Nakai used in the present invention are processed using a medicinal herb processing technique of roasting honeyed medicinal herbs. In the roasting technique, boiled honey is diluted in a suitable amount of warm water, and medicinal herbs are sprayed with, or immersed in, the honeyed water (for 30 minutes to 3 hours), roasted with a weak fire to a specified extent (at a temperature of 100-180° C. for about 10 minutes to 1 hour), and dried. Generally, 25-30 kg of honey is used per 100 kg of medicinal herbs.

In a preferred embodiment of the present invention, honey is added to each of *Adenophora triphylla* var. *japonica* Hara and *Angelica tenuissima* Nakai in an amount of 20-30 wt % based on the weight of the respective medicinal herb and allowed to absorb into the medicinal herb for about 30 minutes to 1 hour. The honeyed medicinal herb is roasted at a temperature of 100 to 180° C. for about 10 minutes to 1 hour. Herein, the temperature and time in the roasting technique are not limited to the above-specified temperature and time and can be easily selected by a person skilled in the art.

b) Step of Obtaining Extracts

The dried *Adenophora triphylla* var. *japonica* Hara and *Angelica tenuissima* Nakai processed in step a), together with dried *Paeonia suffruticosa* Andrews or *Lycium chinense* Mill., are added to water or an organic solvent, extracted under reflux and dipped. Then, the extract is filtered through filter cloth and centrifuged to separate into a residue and a filtrate. The separated filtrate is concentrated under reduced pressure, thus obtaining extracts of honey-roasted *Adenophora triphylla* var. *japonica* Hara and honey-roasted *Angelica tenuissima* Nakai and a herbal extract of *Paeonia suffruticosa* Andrews or *Lycium chinense* Mill.

The organic solvent that is used in the present invention can be selected from the group consisting of ethanol, methanol, butanol, ether, ethyl acetate, chloroform, and mixtures of these organic solvents with water. Preferably, 80% ethanol is used.

Hereinafter, the extraction temperature is preferably 10-80° C. and the extraction time is preferably 6-24 hours. If the extraction temperature and time are outside these specified ranges, extraction efficiency can be reduced or changes in the components of the extracts can occur.

After obtaining the extract using the solvent as described above, the extract may be macerated at room temperature according to a conventional method known in the art, and the macerated extract may be heated and filtered, thus obtaining a liquid-phase material. The liquid-phase material may additionally be evaporated, spray-dried or freeze-dried, thus obtaining an extract.

In the cosmetic composition of the present invention, either a mixture of extracts of honey-roasted *Adenophora triphylla* var. *japonica* Hara and honey-roasted *Angelica tenuissima* Nakai, or a mixture containing an extract of at least one of *Paeonia suffruticosa* Andrews and *Lycium chinense* Mill. in addition to the mixture of extracts of honey-roasted *Adenophora triphylla* var. *japonica* Hara and honey-roasted *Angelica tenuissima* Nakai, is contained in an amount of 0.0001-30 wt % based on the total weight of the composition. If the content of the mixture in the cosmetic composition is less than 0.0001 wt %, the desired effects of the extracts cannot be obtained, and if the content exceeds 30 wt %, a further increase in the content will not lead to a significant increase in the effects of the extracts.

Further, the mixture of the extracts in the cosmetic composition of the present invention contains, based on the total weight of the mixture, 30-70 wt % of the honey-roasted *Adenophora triphylla* var. *japonica* Hara extract, 30-70 wt % of the honey-roasted *Angelica tenuissima* Nakai extract, 10-20 wt % of the *Paeonia suffruticosa* Andrews extract and 10-20 wt % of the *Lycium chinense* Mill extract. Preferably, the mixture contains the honey-roasted *Adenophora triphylla* var. *japonica* Hara extract, the honey-roasted *Angelica tenuissima* Nakai extract, *Lycium chinense* Mill extract and the *Paeonia suffruticosa* Andrews extract at a ratio of 2-4:2-4:1:1.

The cosmetic composition of the present invention contains the above-described medicinal herb extracts as active ingredients and exhibits excellent antioxidant and skin-moisturizing effects.

Advantageous Effects of Invention

The cosmetic composition of the present invention contains either a mixture of extracts of honey-roasted *Adenophora triphylla* var. *japonica* Hara and honey-roasted *Angelica tenuissima* Nakai or a mixture containing an extract of *Lycium chinense* Mill. or *Paeonia suffruticosa* in addition to the extracts of the honey-roasted plants, and thus shows excellent antioxidant and skin-moisturizing effects.

BEST MODE FOR CARRYING OUT THE INVENTION

Hereinafter, the present invention will be described in further detail with reference to examples and test examples. It is to be understood, however, that these examples and test examples are for illustrative purposes only and are not to be construed to limit the scope of the present invention.

PREPARATION EXAMPLE 1

Preparation of Extract of *Adenophora triphylla* var. *japonica* Hara 1 kg of dried *Adenophora triphylla* var. *japonica* Hara was added to 5 l of 80% ethanol aqueous solution, extracted three times under reflux, and then dipped at 15° C. for 1 day. The extract was filtered through filter cloth and centrifuged to separate into a residue and a filtrate. The separated filtrate was concentrated under reduced pressure, thus obtaining 300 g of an extract of *Adenophora triphylla* var. *japonica* Hara.

PREPARATION EXAMPLE 2

Preparation of Extract of *Angelica tenuissima* Nakai 1 kg of dried *Angelica tenuissima* Nakai was added to 5 l of 80% ethanol aqueous solution, extracted three times under reflux, and then dipped at 15° C. for 1 day. The extract was filtered through filter cloth and centrifuged to separate into a residue and a filtrate. The separated filtrate was concentrated under reduced pressure, thus obtaining 250 g of an extract of *Angelica tenuissima* Nakai.

PREPARATION EXAMPLE 3

Preparation of Extract of *Lycium chinense* Mill 1 kg of dried *Lycium chinense* Mill. was added to 5 l of 80% ethanol aqueous solution, extracted three times under reflux, and then dipped at 15° C. for 1 day. The extract was filtered through filter cloth and centrifuged to separate into a residue and a filtrate. The separated filtrate was concentrated under reduced pressure, thus obtaining 215 g of an extract of *Lycium chinense* Mill.

PREPARATION EXAMPLE 4

Preparation of Extract of *Paeonia suffruticosa*

1 kg of dried *Paeonia suffruticosa* was added to 5 l of 80% ethanol aqueous solution, extracted three times under reflux, and then dipped at 15° C. for 1 day. The extract was filtered through filter cloth and centrifuged to separate into a residue and a filtrate. The separated filtrate was concentrated under reduced pressure, thus obtaining 215 g of an extract of *Paeonia suffruticosa*.

PREPARATION EXAMPLE 5

Preparation of Extract of Honey-roasted *Adenophora triphylla* var. *japonica* Hara 300 g (20-30 wt % based on the weight of medicinal herb used) of honey was absorbed into 1 kg of dried *Adenophora triphylla* var. *japonica* Hara. Then, the medicinal herb was roasted at 150° C. for 15 minutes and dried in the shade. The honey-roasted medicinal herb was added to 5 l of 80% ethanol aqueous solution, extracted three times under reduced pressure, and then dipped at 15° C. for 1 day. Then, the extract was filtered through filter cloth and centrifuged to separate into a residue and a filtrate. The separated filtrate was concentrated under reduced pressure, thus obtaining 400 g of an extract of honey-roasted *Adenophora triphylla* var. *japonica* Hara.

PREPARATION EXAMPLE 6

Preparation of Extract of Honey-roasted *Angelica tenuissima* Nakai 300 g (20-30 wt % based on the weight of medicinal herb used) of honey was absorbed into 1 kg of dried *Angelica tenuissima* Nakai. Then, the medicinal herb was roasted at 150° C. for 15 minutes and dried in the shade. The honey-roasted medicinal herb was added to 5 l of 80% ethanol aqueous solution, extracted three times under reduced pressure, and then dipped at 15° C. for 1 day. Then, the extract was filtered through filter cloth and centrifuged to separate into a residue and a filtrate. The separated filtrate was concentrated under reduced pressure, thus obtaining 350 g of an extract of honey-roasted *Angelica tenuissima* Nakai.

PREPARATION EXAMPLE 7

Preparation of Extract of Honey-roasted *Lycium chinense* Mill 300 g (20-30 wt % based on the weight of medicinal herb used) of honey was absorbed into 1 kg of dried *Lycium chinense* Mill. Then, the medicinal herb was roasted at 150° C. for 15 minutes and dried in the shade. The honey-roasted medicinal herb was added to 5 l of 80% ethanol aqueous solution, extracted three times under reduced pressure, and then dipped at 15° C. for 1 day. Then, the extract was filtered through filter cloth and centrifuged to separate into a residue and a filtrate. The separated filtrate was concentrated under reduced pressure, thus obtaining 270 g of an extract of honey-roasted *Lycium chinense* Mill.

PREPARATION EXAMPLE 8

Preparation of Extract of Honey-roasted *Paeonia suffruticosa*

300 g (20-30 wt % based on the weight of medicinal herb used) of honey was absorbed into 1 kg of dried *Paeonia suffruticosa*. Then, the medicinal herb was roasted at 150° C. for 15 minutes and dried in the shade. The honey-roasted medicinal herb was added to 5 l of 80% ethanol aqueous solution, extracted three times under reduced pressure, and then dipped at 15° C. for 1 day. Then, the extract was filtered through filter cloth and centrifuged to separate into a residue and a filtrate. The separated filtrate was concentrated under reduced pressure, thus obtaining 320 g of an extract of honey-roasted *Paeonia suffruticosa*.

PREPARATION EXAMPLE 9

Preparation of Mixed Extract 1

The dried *Adenophora triphylla* var. *japonica* Hara, *Angelica tenuissima* Nakai, *Lycium chinense* Mill and *Paeonia suffruticosa* were mixed together at a weight ratio of 1:1:1:1 to prepare 2 kg of the mixture. The mixture was added to 5 l of 80% ethanol aqueous solution, extracted three times under reflux, and then dipped at 15° C. for 1 day. Then, the extract was filtered through filter cloth and centrifuged to separate into a residue and a filtrate. The separated filtrate was concentrated under reduced pressure, thus obtaining 200 g of a mixed herbal extract.

PREPARATION EXAMPLE 10

Preparation of Mixed Extract 2

The dried *Adenophora triphylla* var. *japonica* Hara, *Angelica tenuissima* Nakai, *Lycium chinense* Mill and *Paeonia suffruticosa* were mixed together at a weight ratio of 3:3:1:1 to prepare 2 kg of the mixture. The mixture was added to 5 l of 80% ethanol aqueous solution, extracted three times under reflux, and then dipped at 15° C. for 1 day. Then, the extract was filtered through filter cloth and centrifuged to separate into a residue and a filtrate. The separated filtrate was concentrated under reduced pressure, thus obtaining 230 g of a mixed herbal extract.

PREPARATION EXAMPLE 11

Preparation of Mixed Extract 3

The honey-roasted *Adenophora triphylla* var. *japonica* Hara, honey-roasted *Angelica tenuissima* Nakai, honey-roasted *Lycium chinense* Mill and honey-roasted *Paeonia suffruticosa* prepared in Preparation Examples 5, 6, 7 and 8, respectively, were mixed together at a weight ratio of 1:1:1:1 to prepare 2 kg of the mixture. The mixture was added to 5 l of 80% ethanol aqueous solution, extracted three times under reflux, and then dipped at 15° C. for 1 day. Then, the extract was filtered through filter cloth and centrifuged to separate into a residue and a filtrate. The separated filtrate was concentrated under reduced pressure, thus obtaining 260 g of a mixed herbal extract.

EXAMPLE 1

Preparation of Mixed Extract 4

The honey-roasted *Adenophora triphylla* var. *japonica* Hara and honey-roasted *Angelica tenuissima* Nakai prepared in Preparation Examples 5 and 6, respectively, were mixed together at a weight ratio of 1:1 to prepare 2 kg of the mixture. Then, the mixture was added to 5 l of 80% ethanol aqueous solution, extracted three times under reflux, and then dipped at 15° C. for 1 day. Then, the extract was filtered through filter cloth and centrifuged to separate into a residue and a filtrate. The separated filtrate was concentrated under reduced pressure, thus obtaining 350 g of a mixed herbal extract.

EXAMPLE 2

Preparation of Mixed Extract 5

The honey-roasted *Adenophora triphylla* var. *japonica* Hara and honey-roasted *Angelica tenuissima* Nakai prepared in Preparation Examples 5 and 6, respectively, and *Lycium chinense* Mill were mixed together at a weight ratio of 3:3:1 to prepare 2 kg of the mixture. The mixture was added to 5 l of 80% ethanol aqueous solution, extracted three times under reflux, and then dipped at 15° C. for 1 day. Then, the extract was filtered through filter cloth and centrifuged to separate into a residue and a filtrate. The separated filtrate was concentrated under reduced pressure, thus obtaining 335 g of a mixed herbal extract.

EXAMPLE 3

Preparation of Mixed Extract 6

The honey-roasted *Adenophora triphylla* var. *japonica* Hara and honey-roasted *Angelica tenuissima* Nakai prepared in Preparation Examples 5 and 6, respectively, and *Paeonia suffruticosa* were mixed together at a weight ratio of 3:3:1 to prepare 2 kg of the mixture. The mixture was added to 5 l of 80% ethanol aqueous solution, extracted three times under reflux, and then dipped at 15° C. for 1 day. Then, the extract was filtered through filter cloth and centrifuged to separate into a residue and a filtrate. The separated filtrate

EXAMPLE 4

Preparation of Mixed Extract 7

The honey-roasted *Adenophora triphylla* var. *japonica* Hara and honey-roasted *Angelica tenuissima* Nakai prepared in Preparation Examples 5 and 6, respectively, *Lycium chinense* Mill and *Paeonia suffruticosa* were mixed together at a weight ratio of 3:3:1:1 to prepare 2 kg of the mixture. The mixture was added to 5 l of 80% ethanol aqueous solution, extracted three times under reflux, and then dipped at 15° C. for 1 day. Then, the extract was filtered through filter cloth and centrifuged to separate into a residue and a filtrate. The separated filtrate was concentrated under reduced pressure, thus obtaining 248 g of a mixed herbal extract.

TEST EXAMPLE 1

Test of Antioxidant Effect (DPPH Test)

To confirm the antioxidant effect of the composition according to the present invention, the DPPH oxidation inhibitory effect of the composition was measured. As a control, the synthetic antioxidant Trolox was used.

A method of evaluating antioxidant activity based on the change in absorbance caused by the reduction of the organic radical DPPH (1,1-diphenyl-2-picrylhydrazyl), in which the antioxidant is oxidized, was used. For the extracts and mixtures obtained in Preparation Examples 1-11 and the mixtures obtained in Examples 1-4, the decrease in absorbance caused by the inhibition of oxidation of DPPH compared to the control was measured, and the concentration at which the absorbance was 50% of the control was defined as the effective antioxidant concentration.

10 µl of each of the samples obtained in Preparation Examples 1-11 and Examples 1-4 was added to 190 µl of a solution of 100 µM DPPH in ethanol to prepare a reaction solution. The reaction solution was allowed to react at 37° C. for 30 minutes, and then measured for absorbance at 540 nm. As a control sample, the widely used synthetic antioxidant Trolox was used. The results of DPPH analysis of each sample are shown in Table 1 below. In Table 1, $IC_{50}$ means the sample concentration at which the absorbance is reduced by 50%.

TABLE 1

| DPPH analysis results (inhibition %) | |
| --- | --- |
| Sample | $IC_{50}$(ppm) |
| Trolox | 65 |
| Preparation Example 1 | 120 |
| Preparation Example 2 | 175 |
| Preparation Example 3 | 180 |
| Preparation Example 4 | 136 |
| Preparation Example 5 | 129 |
| Preparation Example 6 | 130 |
| Preparation Example 7 | 195 |
| Preparation Example 8 | 156 |
| Preparation Example 9 | 164 |
| Preparation Example 10 | 177 |
| Preparation Example 11 | 149 |
| Example 1 | 110 |
| Example 2 | 86 |
| Example 3 | 98 |
| Example 4 | 58 |

TABLE 1-continued

As can be seen in Table 1 above, the mixtures of Examples 1-4 prepared by mixing the herbal extracts at suitable ratios according to the present invention showed excellent antioxidant effects compared to Preparation Examples 1-11. Particularly, the mixture of Example 4 prepared by mixing the honey-roasted *Adenophora triphylla* var. *japonica* Hara, honey-roasted *Angelica tenuissima* Nakai, *Lycium chinense* Mill and *Paeonia suffruticosa* extracts at a suitable ratio showed the greatest antioxidant effect. In addition, the mixture of Example 4 showed very high antioxidant activity compared to the synthetic antioxidant Trolox.

TEST EXAMPLE 2

Confirmation of PPARs Activation

Human keratinocyte HaCaT cells were subcultured in 10% fetal bovine serum-containing DMEM medium, which is a phenol red-free medium, in order to eliminate the effect caused by the phenol red's estrogen. The following three different plasmids were used: a plasmid having PPARα, PPARβ/δ and PPARγ genes downstream of a universal promoter which is expressed in general culture conditions; a plasmid having a PPARs response element ("PPRE") promoter, that is activated by binding with ligand-bound PPARs, and a firefly luciferase gene reporter downstream of the promoter; and a reference plasmid having a β-galactosidase gene bound to a universal promoter (Proc. Natl. Acad. Sci. USA, 91 (1994) 7355-7359).

HaCaT cells were seeded into a 24-well plate at a density of $5 \times 10^4$ cells/well, cultured for 24 hours, and then transiently transfected with the plasmid genes. After 24 hours of culture, the cells were washed with phosphate buffered saline (PBS), and then treated with a specified concentration of 7,3',4'-trihydroxyisoflavone and with a specified concentration of known PPARs ligand (the PPARα ligand Wy-14,643 or the PPARγ ligand troglitazone ("TGZ")) as a positive control group. As a negative control group, a group treated with ethanol used to dissolve the samples was used. After 24 hours of culture, the cells were washed with PBS, harvested and measured for luciferase activity. The measurement results are shown in Tables 1~2 and FIGS. 1~2.

TABLE 2

| | Concentration | luciferase activity |
| --- | --- | --- |
| Control | | 100 |
| WY-14643 | 10 uM | 300 |
| Prep 1 | 10 ppm | 104 |
| Prep 2 | 10 ppm | 124 |
| Prep 3 | 10 ppm | 114 |
| Prep 4 | 10 ppm | 113 |
| Prep 5 | 10 ppm | 115 |
| Prep 6 | 10 ppm | 123 |
| Prep 7 | 10 ppm | 128 |
| Prep 8 | 10 ppm | 108 |
| Ex 1 | 10 ppm | 138 |
| Ex 2 | 10 ppm | 164 |

TABLE 2-continued

|  | Concentration | luciferase activity |
|---|---|---|
| Ex 3 | 10 ppm | 198 |
| Ex 4 | 10 ppm | 276 |

TABLE 3

|  | Concentration | luciferase activity |
|---|---|---|
| Control |  | 100 |
| TGZ | 10 uM | 300 |
| Prep 1 | 10 ppm | 104 |
| Prep 2 | 10 ppm | 124 |
| Prep 3 | 10 ppm | 114 |
| Prep 4 | 10 ppm | 113 |
| Prep 5 | 10 ppm | 115 |
| Prep 6 | 10 ppm | 123 |
| Prep 7 | 10 ppm | 128 |
| Prep 8 | 10 ppm | 108 |
| Ex 1 | 10 ppm | 159 |
| Ex 2 | 10 ppm | 185 |
| Ex 3 | 10 ppm | 198 |
| Ex 4 | 10 ppm | 286 |

Figure 1:
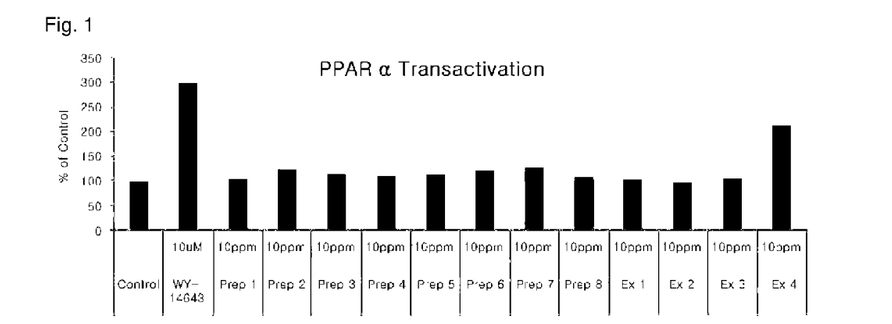
FIG. 1 shows the results obtained by transfecting HaCaT cells, used in the present invention, with a PPRE promoter/reporter plasmid and a PPARα expression plasmid, treating the transfected cells with medicines and measuring the luciferase activity of the cells (Prep: Preparation Example, Ex: Example).

Table 2 and FIG. 1 show the results obtained by transfecting the HaCaT cells, used in this experiment, with the PPRE promoter/reporter plasmid and the PPARα expression plasmid, treating the transfected cells with the medicines and measuring the luciferase activity of the cells. Table 3 and FIG. 2 shows the results obtained by transfecting the cells with both the PPARγ expression plasmid and the PPRE promoter/reporter plasmid, treating the transfected cells with the medicines and measuring the luciferase activity of the cells.

Figure 2:
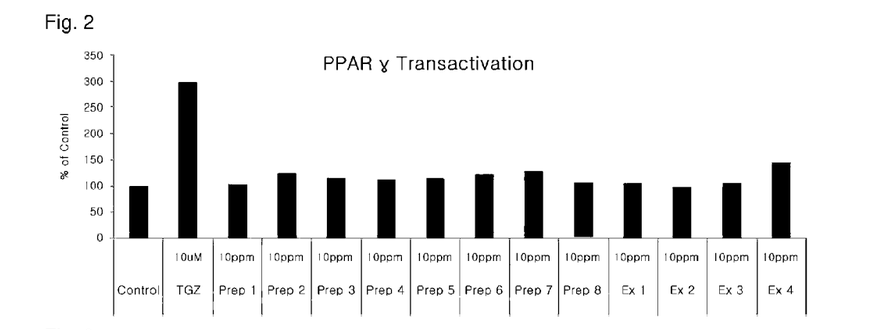
FIG. 2 shows the results obtained by transfecting HaCaT cells with a PPARγ expression plasmid and a PPRE promoter/reporter plasmid, treating the transfected cells with medicines and measuring the luciferase activity of the cells (Prep: Preparation Example, Ex: Example).

The first column of each of the graphs in FIGS. 1 and 2 shows the luciferase activity of the group treated with ethanol as the negative control group, and the second column shows the luciferase activity of the positive control group treated with the PPARα ligand Wy-14,643 or the PPARγ ligand troglitazone as the positive control group.

As can be seen in Tables 1~2 and FIGS. 1~2, the mixtures of Examples 1-4 obtained by mixing the herbal extracts at suitable ratios induced a significantly high degree of PPARα and PPARγ activities compared to Preparation Examples 1-11, and thus showed high liciferase activities compared to Preparation Examples 1-11. Particularly, the mixture of Example 4 obtained by mixing the honey-roasted *Adenophora triphylla* var. *japonica* Hara, honey-roasted *Angelica tenuissima* Nakai, *Lycium chinense* Mill and *Paeonia suffruticosa* extracts at a suitable ratio showed the highest luciferase activity.

TEST EXAMPLE 3

Effect of Promoting Differentiation of Keratinocytes

In order to examine the effects of the samples on the promotion of differentiation of keratinocytes, the cornified envelopes produced during the differentiation of keratinocytes was measured by absorbance in the following manner.

First, human keratinocytes that had been primarily cultured after isolation from the epidermis of infants were placed in a culture flask and attached to the bottom thereof. Then, the culture solution was treated with 1 ppm of each of the test materials shown in Table 4 below, and the cells were cultured for 5 days to a confluence of about 70-80%. A low calcium (0.03 mM)-treated group and a low calcium (1.2 mM)-treated group were used as a negative control group and a positive control group, respectively. The harvested cells were harvested, washed with PBS (phosphate buffered saline), and 1 ml of 10 mM Tris-HCl buffer (pH 7.4) containing 2% SDS (sodium dodecyl sulfate) and 20 mM DTT (dithiothreitol) was added thereto. Then, the cells were sonicated, boiled and centrifuged, and the precipitate was suspended in 1 ml of PBS and measured for absorbance at 340 nm. A portion of the solution obtained after the sonication was taken, and the protein content thereof was measured and used as a reference for evaluating the differentiation of the cells. The test results are shown in Table 4 below.

TABLE 4

| Test materials | Differentiation Capacity (%) of Keratinocytes |
|---|---|
| Low Calcium (0.03 mM) Solution (Negative Control Group) | 100 |
| High Calcium (1.2 mM) Solution (Positive Control Group) | 210 |
| Preparation Example 1 | 120 |
| Preparation Example 2 | 111 |
| Preparation Example 3 | 112 |
| Preparation Example 4 | 111 |
| Preparation Example 5 | 115 |
| Preparation Example 6 | 112 |
| Preparation Example 7 | 115 |
| Preparation Example 8 | 113 |
| Preparation Example 9 | 134 |
| Preparation Example 10 | 121 |
| Preparation Example 11 | 123 |
| Example 1 | 145 |
| Example 2 | 164 |
| Example 3 | 159 |
| Example 4 | 187 |

As can be seen in Table 4, the mixtures of Examples 1-4 obtained by the herbal extracts at suitable ratios significantly promoted the differentiation of ketatinocytes compared to Preparation Examples 1-11. Particularly, the mixture of Example 4 showed the greatest ability to promote the differentiation of kerationocytes.

TEST EXAMPLE 4

Measurement of Effects of Restoring Skin Barrier Function and Increasing Skin Water-holding Capacity in Hairless Mouse Skin In order to measure the effects of the samples on the restoration of skin barrier function damaged due to skin damage and on the increase in the skin's water-holding capacity, the following test was carried out.

First, acetone was applied to the back of 8-10-week-old hairless mice (Charles River, Japan) twice a day for 5 days to induce the loss of skin barrier function in the back of the test animals. Then, the transepidermal water loss (TEWL) of the skin of the test animals was measured with an evaporimeter, and only test animals having skins showing a transepidermal water loss of more than 40 g/m$^2$/hr were selected. To the selected test animals, each of a 7:3 mixture of propylene glycol and ethanol (a vehicle-treated group) and a sample containing 1 wt % of each of Examples 1-4 and Preparation Examples 1-11 was applied in an amount of 200 μl per 5 cm$^2$ of sample area twice a day for 3 days, while the TEWL of the skin was measured at given time intervals. The measurement results are shown in Table 5 and FIG. 3.

TABLE 5

| | Time (h) | | | | | |
| --- | --- | --- | --- | --- | --- | --- |
| | 0 | 6 | 12 | 24 | 48 | 72 |
| Vehicle | 44.3 | 42.5 | 38.7 | 23.5 | 19.7 | 16.3 |
| Ex 1 | 44.9 | 41.4 | 28.5 | 15.4 | 10.4 | 7.5 |
| Ex 2 | 43.5 | 40.4 | 27.3 | 16.4 | 11.4 | 8.5 |
| Ex 3 | 44.5 | 41.4 | 27.7 | 15.2 | 11.1 | 7.1 |
| Ex 4 | 44.8 | 38.1 | 21.5 | 13.2 | 8.9 | 5.4 |
| Prep 1 | 44.8 | 43.5 | 36.7 | 28.5 | 21.7 | 19.4 |
| Prep 2 | 45.1 | 44.9 | 39.5 | 32.8 | 29.3 | 18.3 |
| Prep 3 | 44.5 | 41.1 | 38.4 | 21.1 | 16.4 | 14.2 |
| Prep 4 | 44.7 | 43.2 | 36.5 | 22.6 | 18.6 | 15.5 |
| Prep 5 | 44.5 | 42.5 | 35.6 | 20.2 | 15.4 | 13.1 |
| Prep 6 | 46.8 | 44.5 | 36.2 | 23.5 | 21.7 | 19.8 |
| Prep 7 | 45.8 | 43.9 | 40.5 | 32.8 | 28.3 | 18.9 |
| Prep 8 | 44.5 | 41.1 | 38.4 | 22.3 | 18.6 | 15.2 |
| Prep 9 | 46.7 | 43.2 | 32.5 | 24.6 | 18.6 | 15.9 |
| Prep 10 | 44.5 | 42.5 | 37.5 | 27.5 | 15.4 | 13.6 |
| Prep 11 | 45.1 | 44.9 | 39.5 | 34.5 | 29.3 | 18.7 |

Figure 4:
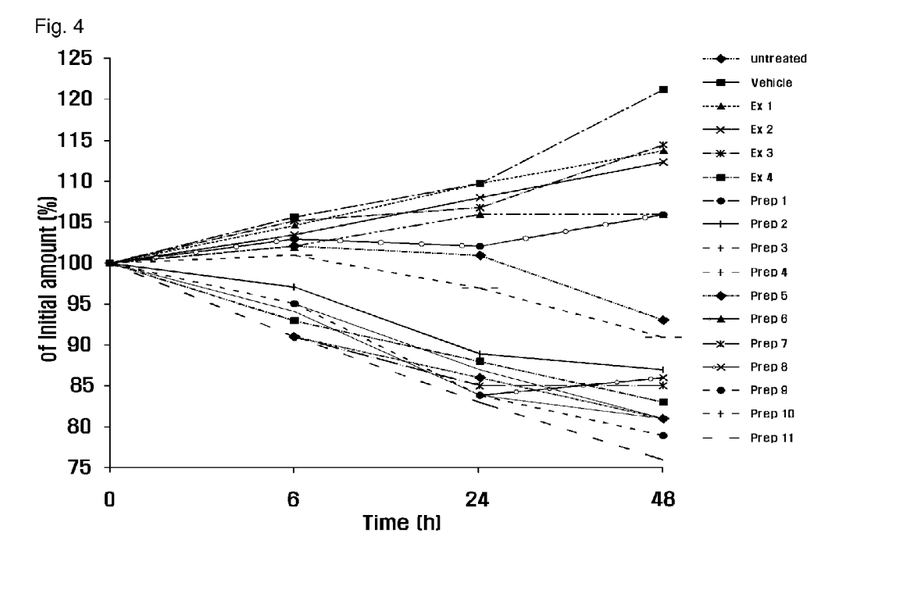
FIG. 4 is a graphic diagram showing the effect of a mixture of herbal extracts according to the present invention on the skin's water-holding capacity (Prep: Preparation Example, Ex: Example).

In addition, the skin's water content was measured with Corneometer (Courage Khazaka, Germany), and the measurement results are shown in Table 6 and FIG. 4. The skin's water content of an untreated group was also measured.

TABLE 6

| | Time (h) | | | |
| --- | --- | --- | --- | --- |
| | 0 | 6 | 24 | 48 |
| untreated | 100 | 91 | 86 | 81 |
| vehicle | 100 | 93 | 88 | 83 |
| Ex 1 | 100 | 104.5 | 109.7 | 113.8 |
| Ex 2 | 100 | 103.5 | 107.9 | 112.4 |
| Ex 3 | 100 | 105.1 | 106.8 | 114.5 |
| Ex 4 | 100 | 105.6 | 109.6 | 121.2 |
| Prep 1 | 100 | 103 | 102 | 106 |
| Prep 2 | 100 | 97 | 89 | 87 |
| Prep 3 | 100 | 95 | 87 | 81 |
| Prep 4 | 100 | 101 | 97 | 91 |
| Prep 5 | 100 | 102 | 101 | 93 |
| Prep 6 | 100 | 102 | 106 | 106 |
| Prep 7 | 100 | 91 | 85 | 85 |
| Prep 8 | 100 | 94 | 84 | 86 |
| Prep 9 | 100 | 95 | 84 | 79 |
| Prep 10 | 100 | 94 | 84 | 81 |
| Prep 11 | 100 | 91 | 83 | 76 |

Figure 3:
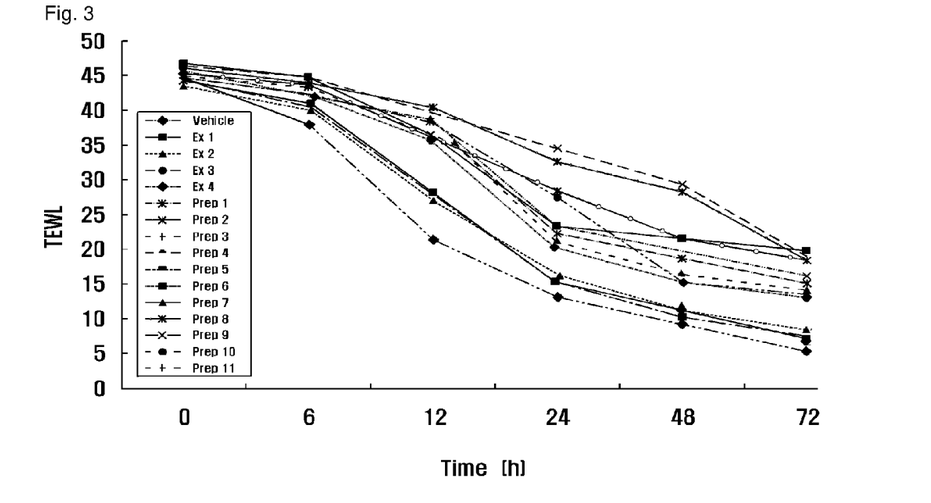
FIG. 3 is a graphic diagram showing the effect of a mixture of herbal extracts according to the present invention on the restoration of damaged skin barrier (Prep: Preparation Example, Ex: Example).

As can be seen in Table 5 and FIG. 3, the skin barrier damage was restored faster in the groups treated with Examples 1-4 than in the vehicle-treated group and the groups treated with Preparation Examples 1-11. Particularly, Example 4 showed the greatest effect of restoring skin barrier damage.

In addition, as shown in Table 6 and FIG. 4, the skin's water content was higher in the groups treated with Examples 1-4 than in the vehicle-treated group and the groups treated with Preparation Examples 1-11.

Accordingly, it can be seen that, if the skin is treated with the mixture of Examples 1-4, the skin barrier damage will be restored more quickly and the skin's water content will be increased.

The results of Test Examples 1-4 suggest that the composition of the present invention can promote the formation of keratinocytes, such that the horny layer can exhibit normal skin barrier function, thereby increasing the water-holding capacity of the skin.

The invention claimed is:

1. A cosmetic composition containing, as an active ingredient, an alcohol extract of a herbal mixture of honey-roasted *Adenophora triphylla* var. *japonica* Hara, honey-roasted *Angelica tenuissima* Nakai, *Lycium chinense* Mill., and *Paeonia suffruticosa* Andrews, wherein the honey-roasted *Adenophora triphylla* var. *japonica* Hara, the honey-roasted *Angelica tenuissima* Nakai, the *Lycium chinense* Mill., and the *Paeonia suffruticosa* Andrews are mixed as the herbal mixture at a ratio of 3:3:1:1 based on the total weight of the mixture.

2. The cosmetic composition of claim 1, wherein the honey-roasted *Adenophora triphylla* var. *japonica* Hara and the honey-roasted *Angelica tenuissima* Nakai are each contained in an amount of 30-70 wt % based on the total weight of the mixture.

3. The cosmetic composition of claim 1, wherein the *Paeonia suffruticosa* Andrews and the *Lycium chinense* Mill. are each contained in an amount of 10-20 wt % based on the total weight of the mixture.

4. A method for enhancing or improving anti-oxidation capacity of skin, comprising applying to the skin an effective amount of a cosmetic composition containing, as an active ingredient, an alcohol extract of a herbal mixture of honey-roasted *Adenophora triphylla* var. *japonica* Hara, honey-roasted *Angelica tenuissima* Nakai, *Lycium chinense* Mill., and *Paeonia suffruticosa* Andrews, wherein the honey-roasted *Adenophora triphylla* var. *japonica* Hara, the honey-roasted *Angelica tenuissima* Nakai, the *Lycium chinense* Mill., and the *Paeonia suffruticosa* Andrews are mixed as the herbal mixture at a ratio of 3:3:1:1 based on the total weight of the mixture.

5. The method of claim 4, wherein the honey-roasted *Adenophora triphylla* var. *japonica* Hara and the honey-roasted *Angelica tenuissima* Nakai are each contained in an amount of 30-70 wt % based on the total weight of the mixture, and wherein the *Paeonia suffruticosa* Andrews and the *Lycium chinense* Mill. are each contained in an amount of 10-20 wt % based on the total weight of the mixture.

6. A method for enhancing or improving moisturization of skin, comprising applying to the skin an effective amount of a cosmetic composition containing, as an active ingredient, an alcohol extract of a herbal mixture of honey-roasted *Adenophora triphylla* var. *japonica* Hara, honey-roasted *Angelica tenuissima* Nakai, *Lycium chinense* Mill., and *Paeonia suffruticosa* Andrews, wherein the honey-roasted *Adenophora triphylla* var. *japonica* Hara, honey-roasted *Angelica tenuissima* Nakai, the *Lycium chinense* Mill., and the *Paeonia suffruticosa* Andrews are mixed as the herbal mixture at a ratio of 3:3:1:1 based on the total weight of the mixture.

7. The method of claim 6, wherein the honey-roasted *Adenophora triphylla* var. *japonica* Hara and the honey-roasted *Angelica tenuissima* Nakai are each contained in an amount of 30-70 wt % based on the total weight of the mixture, and wherein the *Paeonia suffruticosa* Andrews and the *Lycium chinense* Mill. are each contained in an amount of 10-20 wt % based on the total weight of the mixture.

8. A method of promoting formation of keratinocytes in skin, comprising applying to the skin an effective amount of a cosmetic composition containing, as an active ingredient, an alcohol extract of a herbal mixture of honey-roasted *Adenophora triphylla* var. *japonica* Hara, honey-roasted *Angelica tenuissima* Nakai, *Lycium chinense* Mill., and *Paeonia suffruticosa* Andrews, wherein the honey-roasted *Adenophora triphylla* var. *japonica* Hara, the honey-roasted *Angelica tenuissima* Nakai, the *Lycium chinense* Mill., and the *Paeonia suffruticosa* Andrews are mixed as the herbal mixture at a ratio of 3:3:1:1 based on the total weight of the mixture.

9. The method of claim 8, wherein the honey-roasted *Adenophora triphylla* var. *japonica* Hara and the honey-roasted *Angelica tenuissima* Nakai are each contained in an amount of 30-70 wt % based on the total weight of the mixture, and wherein the *Paeonia suffruticosa* Andrews and the *Lycium chinense* Mill. are each contained in an amount of 10-20 wt % based on the total weight of the mixture.

10. The cosmetic composition of claim 1, wherein the alcohol is ethanol.

11. The cosmetic composition of claim 1, wherein the alcohol is 80% ethanol.

12. The method of claim 4, wherein the alcohol is ethanol.
13. The method of claim 6, wherein the alcohol is ethanol.
14. The method of claim 8, wherein the alcohol is ethanol.

* * * * *